US006872228B1

(12) United States Patent
Lenzi-Brangi et al.

(10) Patent No.: US 6,872,228 B1
(45) Date of Patent: Mar. 29, 2005

(54) HAIR BLEACH PRODUCT

(75) Inventors: Anne Marie Lenzi-Brangi, Orange, CT (US); Mary Larkin, South Salem, NY (US); Stephen Casperson, Milford, CT (US)

(73) Assignee: The Procter & Gamble Company, Cincinnati, OH (US)

( * ) Notice: Subject to any disclaimer, the term of this patent is extended or adjusted under 35 U.S.C. 154(b) by 28 days.

(21) Appl. No.: 10/392,989

(22) Filed: Mar. 20, 2003

Related U.S. Application Data

(60) Provisional application No. 60/368,179, filed on Mar. 28, 2002.

(51) Int. Cl.[7] .................................................. D06L 3/10
(52) U.S. Cl. ..................... 8/110; 8/111; 8/101; 132/221; 424/62
(58) Field of Search ............................. 8/101, 110, 111; 132/221; 424/62

(56) References Cited

U.S. PATENT DOCUMENTS

| | | | |
|---|---|---|---|
| 4,226,852 A | 10/1980 | Tesmann et al. | |
| 4,507,278 A | 3/1985 | DeMarco et al. | |
| 5,688,291 A * | 11/1997 | Said et al. ..................... | 8/431 |
| D394,730 S | 5/1998 | Olsson | |
| 5,964,226 A * | 10/1999 | Sobel ......................... | 132/108 |
| 2002/0139957 A1 | 10/2002 | Matsuo et al. | |

* cited by examiner

*Primary Examiner*—Margaret Einsmann
(74) *Attorney, Agent, or Firm*—Brian M. Bolam; Marianne Dressman; Tara M. Rosnell

(57) ABSTRACT

The present invention relates to a hair bleach product composition having a rheology adapted to maintain the product in a reservoir of an applicator until a shear force is applied by passing the applicator reservoir containing the hair bleach product composition through the hair to be treated.

16 Claims, 2 Drawing Sheets

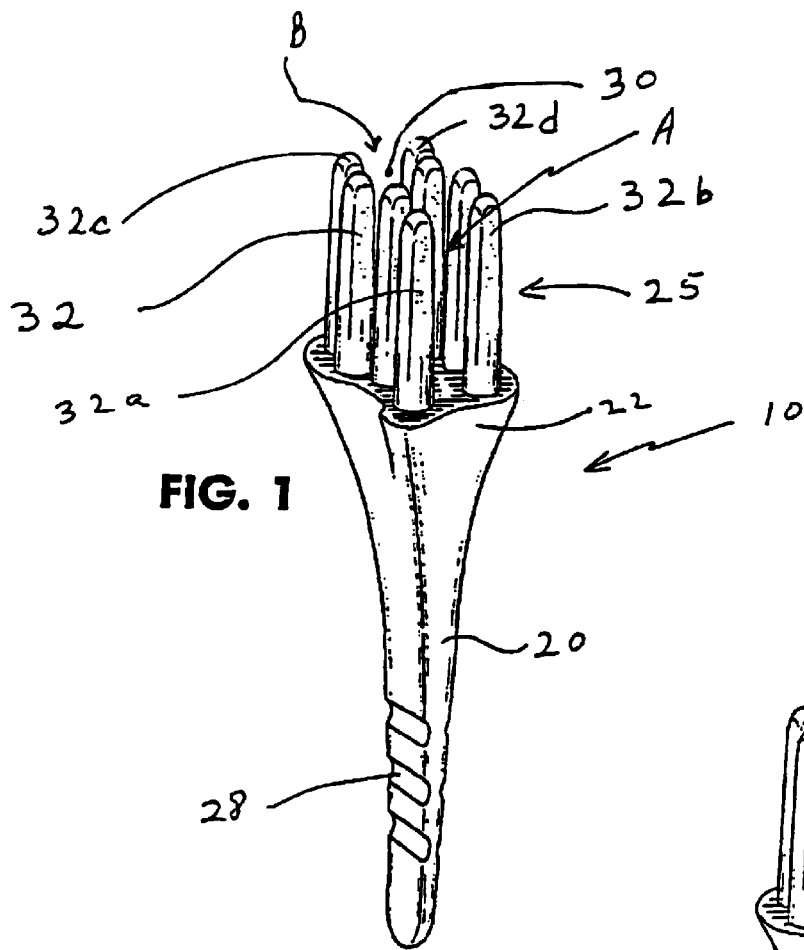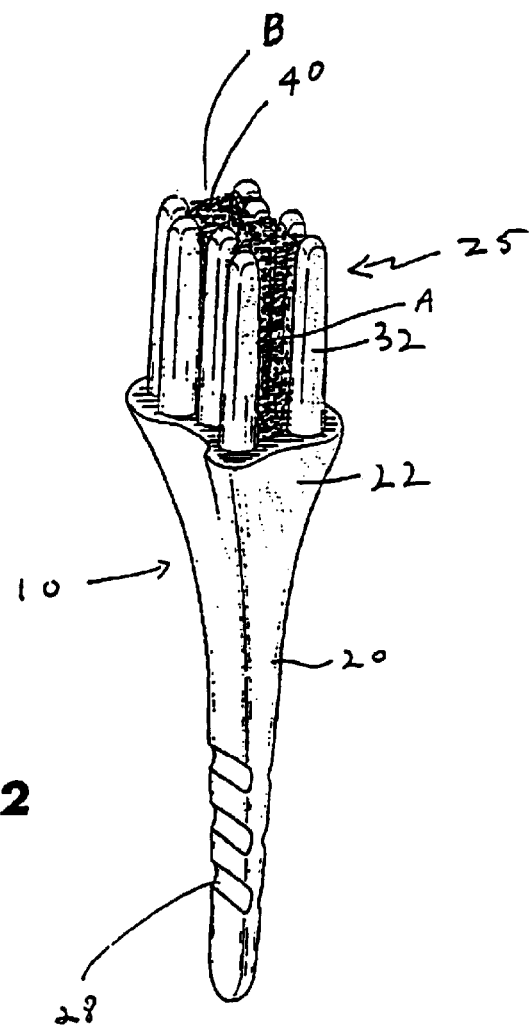

HAIR BLEACH PRODUCT

This patent application claims the benefit of U.S. Provisional Application No. 60/368,179 filed Mar. 28, 2002.

FIELD OF INVENTION

The present invention relates to hair bleach products. Specifically, the invention concerns hair bleach products that comprise in kit form: (A) a three part hair bleaching system comprising (a) peroxide-based developer, (b) a powder activator containing a persulfate oxidizing system, and (c) an alkalizing agent, and (B) an applicator adapted to receive and hold a predetermined amount of the bleach composition in a manner suitable for application to the hair. More specifically, the invention relates to the use of the above-described hair bleach product to provide highlights to the hair of the user.

BACKGROUND OF THE INVENTION

Hair bleaching is a well known process in the hair cosmetic field. Hair bleaching involves the application of an oxidizing agent to the hair for a period of time effective to achieve a desired lighter hair shade. The oxidizing agent typically is a hydrogen peroxide solution in concentrations ranging from 3 to 12% by weight. The hydrogen peroxide is applied to the hair under alkaline pH conditions and gradually lightens the shade of the hair by oxidizing the melanin that gives it color. 28% Ammonium hydroxide is typically added to the peroxide solution at the time of use to provide the highly alkaline environment needed during use.

To enhance the lightening efficacy of the hydrogen peroxide oxidizer, it is known to incorporate a persulfate salt as a "booster". Sodium, potassium, and ammonium persulfate salts, and mixtures thereof are provided in powder form, and are admixed with the hydrogen peroxide solution and the ammonium hydroxide solution at the time of use. The mixed product is then applied to the hair for a period of time effective to achieve the desired lighter hair shade. Because of the incorporation of the persulfate and when used with a 10 to 40% by volume hydrogen peroxide solution activated by the alkalizing agent, e.g., 28% ammonium hydroxide, substantial lightening of hair can be achieved. Such products are typically sold in kit form comprising the three part system comprising the peroxide, activator and alkaline compositions that are admixed at the time of use for form a hair bleach product composition.

The hair bleach product composition is generally applied to the hair with a brush that is dipped into the bleach product composition. To streak or highlight the hair, sections of the hair are individually treated, and the sections are then segregated from the remainder of the hair, e.g., with aluminum foil.

SUMMARY OF THE INVENTION

It is an object of the invention to provide a hair bleach product in kit form comprising: (A) a three part hair bleaching system comprising: (a) a hydrogen peroxide developer composition, (b) a persulfate activator powder composition, and (c) an alkalizing agent composition, the compositions (a), (b) and (c) being admixable at the time of use to form a hair bleach product composition for applying to the hair of the user, and (B) an applicator adapted to receive and hold a predetermined amount of the hair bleach product composition in a manner suitable for application to the hair.

Another object of the present invention is to provide a method for applying highlights to hair.

A further object of the invention is to provide an applicator containing a hair bleach product composition in a reservoir that may be applied to hair.

The hair bleach product of the present invention is in kit form and comprises in separate packages within the kit (a) a peroxide developer composition; (b) a powder activator composition, and (c) an alkalizing agent composition. Together the three packages define a hair bleach system (A). The component parts (a), (b) and (c) of the hair bleach system are admixed at the time of use to provide the hair bleach product composition. The kit further comprises an applicator (B) adapted to receive and hold a predetermined amount of the hair bleach product composition in a volumetric space adapted for transferring the bleach product composition to the hair by passing the hair therethrough.

The peroxide developer composition (a) contains from about 3 to about 12% by weight hydrogen peroxide (corresponding to a 10 to 40 volume solution), which is an oxidizing agent capable of lightening hair to some extent.

The powder activator composition (b) contains from about 40 to about 80% by weight of an alkali metal persulfate selected from the group consisting of sodium persulfate, potassium persulfate, and ammonium persulfate.

The alkalizing agent composition (c) preferably has a thickened liquid, gel, cream or other substantially nonflowing rheology, and contains from about 10 to about 25% by weight of an alkalizing agent selected from the group consisting of ammonium hydroxide and monoethanolamine.

To use the hair bleach system (A), the three components; namely, the developer composition (a), the activator composition (b), and the alkalinity agent composition (c) are admixed together just prior to use. These individual components of the hair bleach system are formulated so that, when admixed, the hair bleach product composition has a rheology such that the product composition exhibits minimal flow in the absence of a shear force, but flows easily when a shear stress is applied. This permits the user to fill the applicator without loss of hair bleach product composition via leaking, dripping, running, etc., and then to apply the hair bleach product composition to the hair with the applicator by passing the applicator containing the product through a preselected section of the hair, whereby the preselected section of the hair will be lightened by the bleaching action of the composition.

BRIEF DESCRIPTION OF THE INVENTION

FIG. 1 is a first embodiment of the applicator contained in the kit of the present invention.

FIG. 2 illustrates the applicator of FIG. 1 containing the hair bleach product composition in the reservoir.

DETAILED DESCRIPTION OF THE INVENTION

Figure 3:
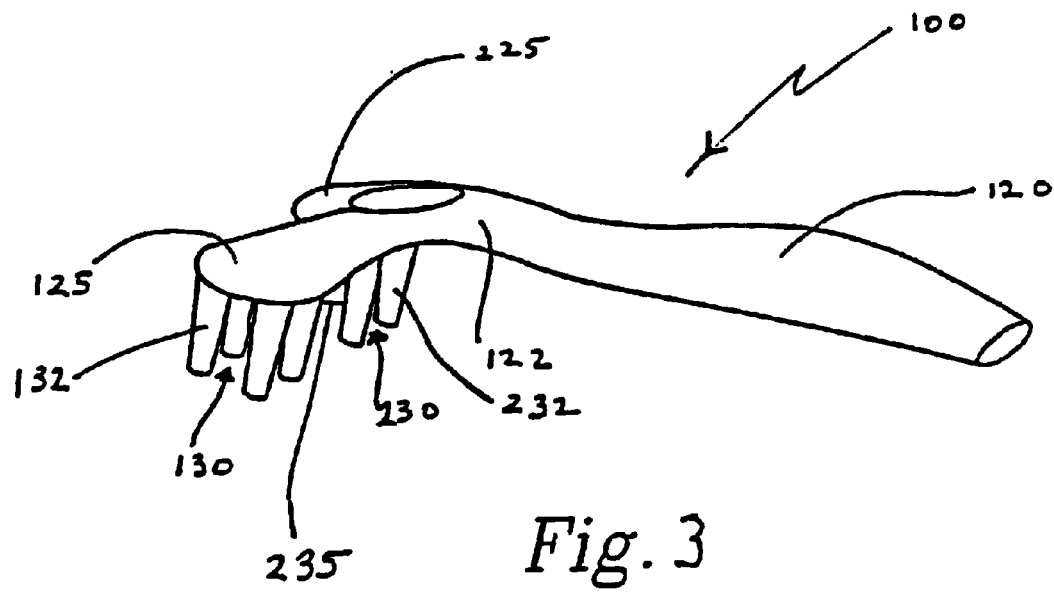
FIG. 3 is a second embodiment of the applicator contained in the kit of the present invention.

The hair bleach product is adapted to provide sufficient lightening within a given period of time so that hair may be bleached to a lighter, and preferably a blonde shade. The hair bleach product of the present invention comprises (A) a three part hair bleaching system comprising (a) a peroxide solution, generally referred to in the field as the developer component; (b) a powder activator component, also referred to in the field as a lightening powder or a booster, and (c) an alkalizing agent component, and (B) an applicator adapted to receive and hold a predetermined amount of the bleach product composition in a volumetric space defined by a plurality of three or more tines (as hereinafter described in greater detail), the bleach product composition being transferable to the hair as the volumetric space is passed therethrough.

These three components (a), (b) and (c) comprising the system (A) and the applicator (B) are typically provided in the form of a kit, which may further include instructions for use, gloves, a hair pretreatment component, and a hair post treatment component. The three essential components (a), (b) and (c) of the hair bleach product kit are admixed at the time of use, typically in a container that is separately part of the kit, or that is provided as the container for one of the three components (a), (b) or (c).

The Developer Component

The developer component composition comprises a hydrogen peroxide solution. The solution contains from about 3 to about 12%, preferably 6 to 12%, most preferably about 9% by weight hydrogen peroxide. (This corresponds to a 10 to 40 volume solution, and is referred to as, e.g., 20 volume, 30 volume or 40 volume hydrogen peroxide. This concentration unit refers to the amount of oxygen released from one volume of the hydrogen peroxide solution. Thus, one volume of a 30 volume peroxide solution is able to liberate 30 volumes of oxygen.)

The developer component composition preferably contains additional ingredients to facilitate its use and performance. Thus, the developer component composition further contains one or more of the following adjuvants: a thickener, an emulsifier, or a hair conditioning agent. Each of these constituents is present in the developer component in sufficient amount to provide its intended function in the developer component composition or in the hair bleach product composition obtained when the developer component is mixed with the activator powder component and the alkalizing agent component. Suitable adjuvants are those that are stable to hydrogen peroxide.

In formulating the developer component and especially in selecting the thickening agent, consideration should be given to the selection of the thickener component(s) that will achieve the requisite rheological and viscosity properties of the hair bleach product composition as hereinafter described. Suitable thickeners are, for example, cetearyl alcohol and stearamidopropyl dimethylamine. Nonionic polymeric thickeners, in particular polyether urethanes sold under the tradename Aculyn by Rohm & Haas Company, especially Aculyn 44 and 46, are suitable. Anionic acrylate polymers, e.g., such polymers sold under the tradename Aculyn, e.g., Aculyn 22, 28 and 33, by Rohm and Haas may be used. Other useful thickeners are fatty alcohols such as stearyl alcohol, cetyl alcohol and cetearyl alcohol and ethoxylated surfactant mixtures such as Nonoxynol 2.5, $C_{12-15}$ Pareth-3 and $C_{12-15}$ Pareth-7. Especially suitable are mixtures of gel forming ethoxylated nonionic surfactants, such mixtures characterized by at least one surfactant with an HLB of less than or equal to 9, preferably from about 1 to about 7.5, and at least one surfactant with an HLB of greater than 9, preferably from about 10 to about 14. Among the low HLB ethoxylated surfactants mention may be made of $C_{12-15}$ Pareth-3, Ceteareth-2, Ceteth-2, Ceteth-5, Laureth-3, Oleth-2, Oleth-5 and Steareth-5. Among the high HLB ethoxylated surfactants mention may be made of $C_{12-13}$ Paraeth-9, Ceteareth-15, Ceteth-12, Laureth-15, Oleth-10, and Steareth-21. Stability in the presence of hydrogen peroxide should to be confirmed with the manufacturers.

Generally, the thickening agents are present in an amount effective to provide a developer component viscosity of from 3,000 to about 40,000 cps, preferably 5,000 to about 30,000 cps. at 25° C. and atmospheric pressure, as measured by a Brookfield LVT viscometer with No. 3 Spindle at 6 rpm. Typically, the thickener is present in an amount ranging from about 0.05% to about 5%, preferably about 0.1 to about 2.5%, depending on the choice of thickener agent and the degree of thickening that is desired.

Emulsifiers, if present in the developer component are typically in the range of from about 0.05 to about 10% preferably from about 0.1 to about 5%, especially 0.5 to 2.5% by weight of the developer composition. Suitable emulsifiers are glyceryl stearate, oleth 2, oleth-10, PEG-75 lanolin and ceteareth-20. Often, mixtures of emulsifiers are employed. The emulsifiers, which are surface active agents, may also contribute to thickening of the composition as noted above. Other emulsifiers are identified in the International Cosmetic Ingredient Dictionary and Handbook, Eighth Edition, v. 2, at pages 1795–1803. Compatability with peroxide should be confirmed.

The developer composition may further contain an antifoam material such as simethicone in low concentration, to prevent foaming during manufacture, an acidifying material, a preservative, etc. while conventional hair conditioning agents, e.g., stearamidopropyl dimethyamine, may be incorporated in the developer if compatible at the acidic conditions and in the presence of hydrogen peroxide. Conditioning agents are generally incorporated in the alkalizer component.

The pH of the developer component is generally in the range of from about 2.5 to about 5.5, especially about 3 to about 4.

The Powder Activator Component

The powder activator component of the present invention comprises an alkali metal persulfate selected from the group consisting of sodium persulfate, potassium persulfate, ammonium persulfate, and mixtures thereof. The powder activator component contains from about 40 to about 80%, preferably 50 to 70%, of the persulfate by weight of the activator component composition. The preferred alkali metal persulfate is a mixture of ammonium persulfate and potassium persulfate. Sodium persulfate may also be used.

The powder activator component further contains an alkalinity agent to ensure an alkaline bleach product when the product components are mixed. Suitably, the alkalinity agent is sodium silicate present in the activation powder component in an amount of from about 20 to about 50% by weight of the powder activator component composition, preferably from about 30 to 40% by weight.

A dessicant such as silica is also typically incorporated to prevent moisture from prematurely reacting with the presulfates. The silica is a positive amount generally less than about 5% by weight, usually from about 0.1% to about 3% by weight of the activator component. A lubricant may be incorporated to assist in dry blending of the powder materials, for example, a surfactant such as sodium lauryl sulfate may be incorporated in an amount of up to about 3% by weight of the composition. Each of the adjuvant constituents is present in the powder activator component in sufficient amount to provide its intended function in the powder activator component composition or in the final product mixture when mixed with the developer and the alkalizing agent.

In formulating the powder activator component the requisite rheological and viscosity properties of the hair bleach product composition as hereinafter described should be taken into account. Thickeners as described in connection with the developer component are not typically incorporated in the powder because such thickeners are typically organic liquids, aqueous dispersions of the active thickener ingredient or have a tacky consistency incompatible with the nature of a free-flowing powder.

The Alkalizing Agent Component

The third essential component of the hair bleach system is the alkalizing agent component The alkalizing agent in the alkalizing agent component is selected from the group consisting of ammonium hydroxide, monoethanolamine, and mixtures thereof.

This component composition generally has a pH of from about 8 to 12, preferably from about 9.5 to 11.5, especially about 10.5 to 11, by incorporating an effective amount of the alkalizing agent to achieve such pH values. Generally, the alkalizing agent is present in an amount of from about 3 to about 25% by weight of the alkalizing agent component, depending upon the alkalizing agent used. For monoethanolamine, the concentration is about 10 to 25% preferably about 12 to about 21% by weight. Where ammonium hydroxide is the alkalizing agent, its concentration in the alkalizer agent component is from about 3 to about 18% by weight, measured as a 28% by weight ammonium hydroxide solution, preferably from about 5 to about 15%. In any event the alkalizing agent is present in an amount effective to obtain the requisite pH set forth above.

Preferably, the alkalizing agent component is in the form of a thickened liquid, a gel or a cream, which form facilitates its admixture with the developer and activator powder components, although aqueous solutions, e.g., thin lotions, can be used.

The adjuvants useful in achieving the desired form of the alkalizing agent component and their incorporation to form the gel, the cream or the thickened liquid are well known to those of ordinary skill in the art. Such useful adjuvants are thickeners, surface active agents, and emulsifiers, all as described above in the section on the developer component Also useful as adjuvants are fragrances, dyes, herbal extracts, and the like.

A gel composition is obtainable using oleic acid, dilinoleic acid and mixtures thereof as a gelling agent and may further include a blend of anionic and nonionic surface active agents. Suitably, the oleic acid gelling agent is present in an amount of from about 0.1 to about 10% by weight of the alkalizing agent component. The surface active agents are typically present in an amount of from about 0.1 to about 15% by weight, depending on the choice of thickening agent and the degree of thickening that is desired.

A cream composition having a viscosity of from about 50,000 to about 700,000 cps, preferably from about 100,000 to about 500,000 cps at 25° C. and atmospheric pressure, as measured by a Brookfield LVT viscometer using a T-D spindle at 6 rpm descending for 60 seconds, can be obtained with a suitable amount of a surfactant thickening system. Useful surfactants are stearamide MEA, cocamide MEA, cetyl alcohol, myristyl alcohol, cetearyl alcohol, behenamidopropyl betaine, and stearamidopropyl betaine. Other thickening agents include the previously mentioned polyether urethane and polyacrylic acid-based polymers.

In formulating the alkalizing agent component and especially in selecting the thickening agent, consideration should be given to the selection of the thickener component(s) that will achieve the requisite rheological and viscosity properties of the hair bleach product composition as hereinafter described. Generally, the polyether urethanes and the acrylate polymers are suitable in providing the requisite rheology. Also suitable are mixtures of gel forming ethoxylated nonionic surfactants, for example $C_{12\text{-}15}$ Pareth-3 and $C_{12\text{-}15}$ Pareth-7, and especially such mixtures characterized by at least one surfactant with an HLB of less than or equal to 9, preferably from about 1 to about 7.5, and at least one surfactant with an HLB of greater than 9, preferably from about 10 to about 14. Among the low HLB ethoxylated surfactants mention may be made of $C_{12\text{-}15}$ Pareth-3, Ceteareth-2, Ceteth-2, Ceteth-5, Laureth-3, Oleth-2, Oleth-5 and Steareth-5. Among the high HLB ethoxylated surfactants mention may be made of $C_{12\text{-}13}$ Pareth-9, Ceteareth-15, Ceteth-12, Laureth-15, Oleth-10, and Steareth-21. Typically, the thickener is present in an amount ranging from about 0.05 to about 10%, preferably from about 0.1 to about 7.5%, depending on the choice of thickening agent and the degree of thickening that is desired.

Conditioning agents may also be incorporated in amounts of from 0.1 to about 10%, preferably 0.5 to 5% by weight of the alkalizing component composition. Suitable conditioners are identified in the International Ingredient Dictionary and Handbook referred to above at v.2, pages 1752–1759 incorporated by reference, in particular betaines, such as cocamidopropyl betaine, and linoleamidopropyl dimethyl amine dimer dilinoleate. Also useful are Polyquaternium 47, sold as Merquat 2001 by Nalco, Inc., and Polyquaternium 22, sold as Merquat 280 by Nalco, Inc.

Generally, the pigment as previously described is not contained in the alkalizing agent component. Because the pigment is insoluble, it would have to be suspended in this component composition, which adds additional complexity during manufacture, as well as difficulties occasioned by precipitation during storage.

The Applicator

The hair bleach kit of the present invention also contains an applicator. The applicator is of the type having a handle, at least one head connected to the handle, and a retaining structure or reservoir for holding the hair bleach product composition (obtained upon admixture of the developer (a), activator (b), and alkalizing agent (c) component compositions), the reservoir being a substantially open volumetric space through which the hair passes during the application of the hair bleach composition. The hair bleach product composition contained in the substantially open volumetric space that is the reservoir is essentially nonflowing in the reservoir and in the absence of shear in light of the thixotropic rheology of the hair bleach product composition.

A suitable applicator having a single reservoir is disclosed in U.S. Des. Pat. No. D393,730 incorporated herein by reference, and is also shown in FIG. 1. A preferred applicator having a plurality of heads is disclosed in U.S. Provisional Patent Application Ser. No. 60/416,163 filed Oct. 4, 2002 and incorporated herein by reference. This applicator is shown in FIG. 3.

The applicator 10 of FIG. 1 comprises a handle 20, a head 25 connected at end 22 of the handle 20, and a reservoir 30 that is a substantially open volumetric space as defined by a plurality of tines 32. In the embodiment shown, six tines 32 are illustrated, but the reservoir may be defined by as few as three tines 32. Preferably, the reservoir will be defined by from four to eight tines 32, with six tines most preferred. Adjacent, peripheral tines define a planar space, e.g., tines 32a and 32b define planar space A and tines 32 and 32d define planar space B, spaces A and B being opposed one to the other. End 22 of the handle has a plurality of notches 28 to assist the user in gripping the applicator.

FIG. 2 illustrates the applicator of FIG. 1 in which hair bleach product composition 40 has been placed within the reservoir 30. The hair bleach product composition is retained in the reservoir 30 in light of its thixotropic rheological properties as hereinafter described. In use, the applicator 10 laden with hair bleach product composition 40 is pulled through the hair to be treated and the hair passes through opposed spaces, e.g., spaces A and B, sequentially.

The applicator 100 of FIG. 3 comprises a handle 120, a first head 125 and a second head 225 both connected at end 122 of the handle 120, and first and second reservoirs 130 and 230 that are substantially open volumetric spaces as defined by the pluralities of tines 132 and 232. In the embodiment shown in FIG. 3, four tines are shown for each reservoir, but the reservoirs may each have as few as three tines. Preferably, each reservoir 130 and 230 will have from four to six tines 132 or 232, as the case may be, with four tines being preferred. Adjacent, peripheral tines define a planar space, e.g., tines 132a and 132b define planar space C and tines 132c and 132d define planar space D, as shown in FIG. 4, spaces C and D being opposed one to the other.

Figure 4:
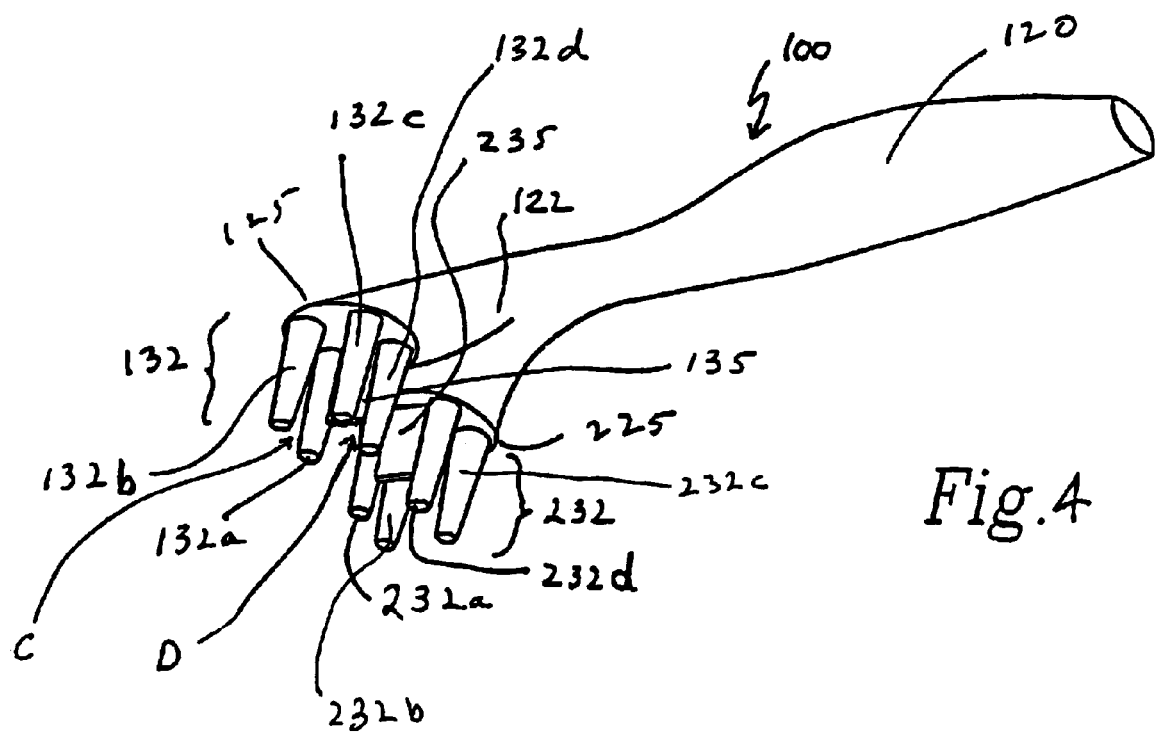
FIG. 4 illustrates the applicator of FIG. 3 in a rotated orientation.

FIG. 4 illustrates a rotated view of the applicator of FIG. 3. Hair bleach product compositions (not shown), which may be the same or different (e.g., compositions with different peroxide levels), but within the scope disclosed herein, are placed, respectively, in reservoirs 130 and 230, analogously to composition 40 shown in FIG. 2. The hair bleach product composition is retained in the reservoirs in light of its thixotropic rheological properties, as hereinafter described. In use, the applicator 100 laden with hair bleach product composition is pulled through the hair to be treated and the hair passes through opposed planar spaces, e.g., planar spaces C and D, sequentially. As most clearly seen in FIG. 4, reservoir 130 is provided with a baffle 135 between tines 132a–132d, which tines are adjacent tines 232a–232d, which in turn are provided therein between with baffle 235 within reservoir 230. These baffles serve to keep product away from hair passing through the region between heads 125 and 235, thereby ensuring formation of two streaks when used.

The Kit

The kit comprises the hair bleach system (A) comprising premeasured amounts of the developer component (a), the powder activator component (b) and the alkalizing agent component (c), and the applicator (B). The kit further comprises instructions for use, gloves, and optionally pre- and/or post-treatments, e.g., a conditioning treatment for the hair.

The developer component (a) is preferably provided in a container which may also serve as the container for mixing the components. Alternatively a separate bowl can be used to admix the components of the hair bleaching system (A). The activator powder component (b) is typically contained in a foil pouch packet, the entire contents of which are emptied by the consumer into the developer component container. Lastly, the alkalizing agent component (c), which preferably is in gel form and contained in a tube, is added to the mixing vessel. The three component compositions are then mixed together.

The hair bleach product composition applied to the hair (i.e., the mixture of the three components) has a rheology such that it sets up when no shear forces are acting upon it, but under moderate shear stress begins to flow but with a viscosity that is sufficiently high to avoid dripping and running down the face and neck of the person having his or her hair lightened. Generally, this rheology is referred to as thixotropic, or shear-thinning. The viscosity of the hair bleach product composition is from about 20,000 to about 60,000 cps, preferably from about 30,000 to about 45,000 cps. at 25° C. and atmospheric pressure as measured by a Brookfield LVT viscometer using an appropriate spindle at a proper speed. The product remains on the hair until the desired lightening of the hair is achieved. Generally, this period of time is less than about 60 minutes, preferably 15 to 45 minutes.

The proportions of the three components used in the process are generally adapted so that there is no excess product or residual components of the product remaining after use. The proportions are predetermined so that the proper consistency of the product and the desired concentrations of the active ingredients as well as the adjuvants separately contained in one or more of the product component compositions are achieved on admixture of the three components, and so that the final product pH will be from about 8 to about 12, preferably from about 9.5 to about 11.5, especially about 10.5 to 11.

The hair bleach product composition must also contain sufficient amount of the thickener such that the requisite rheology and viscosity characteristics described above are achieved. When the thickener is a polyetherurethane or polyacrylic thickener as previously described, the amount of the thickener is generally form 0.05 to 5% by weight of the hair bleach product composition on an active ingredient basis. When a surfactant system is employed to thicken, and especially to form a gel system, the surfactant thickener system would preferably contain by weight of the hair bleach product composition from about 0.1 to about 10%, preferably from about 1 to 5%, of a first ethoxylated surfactant having an HLB of 9 or less, preferably an HLB of from about 1 to about 7.5, and from about 0.1 to about 10%, preferably from about 1 to 5%, of a second ethoxylated surfactant having an HLB above about 9, preferably an HLB of from 10 to about 14, the ratio of the first and second ethoxylated surfactants being such as to obtain the required rheology and viscosity. Of course various thickener types can be used in the same product.

The final bleach product composition, based on mixing of the three essential component compositions comprises on an active ingredient basis:

|  | Range (wt./o) | Preferred Concentration (wt./o) |
| --- | --- | --- |
| Hydrogen Peroxide | 3–7.5 | 4–6 |
| Alkali Metal Persulfate | 3–12 | 5–9 |
| Alkalizing Agent | 2.5–7.5 | 4–6 |

As a hair bleach product suitable to bleach an entire head of hair, the kit typically comprises from about 60 to about 220 ml. developer component; from about 14 to about 56 g. powder activator component; and from about 28 to about 112 g. alkalizing agent component. The kit generally comprises from about 3 to 5 parts developer component per part of activator powder component and from about 1.5 to about 2.5 parts alkalizing agent component per part of activator powder component. In a preferred embodiment 4 parts developer (112 g.), 1 part powder activator (28 g.) and 2 parts alkalizing agent component (56 g.) are mixed to provide the bleach composition applied to the hair. In this embodiment the developer contains about 30 volume hydrogen peroxide (about 9% by weight); the powder activator contains about 60% by weight of persulfates, and the alkalizing agent component contains about 18% by weight alkalizing agent. When provided as highlights product, the amounts for each of the components would be substantially less, typically from about one-tenth to one-half the amounts set forth above, but in the same proportions.

Use of the Bleach Product

As described above the powder activator composition, the developer component, and the alkalizing agent component are added to a mixing vessel, and blended together. When a uniform mixture has been obtained, the hair bleach composition, when all shear forces have been removed, has a paste-like consistency. This composition may be scooped-up and placed into the reservoir (s) of the applicator (B), or applied through a nozzle attached to the mixing vessel and into the applicator reservoir(s). Even though the reservoir of the applicator (B) shown in FIGS. 1 and 2 does not have sidewalls, the hair bleach product composition is retained in the reservoir because of its unique rheology and the absence of shear forces acting upon it. The user then applies the hair bleach product composition to the hair by pulling the applicator, specifically the head of the applicator and its product composition laden reservoir, through the hair in a uniform smooth motion. With the applicator shown e.g., in FIGS. 3 and 4, the hair bleach product composition is applied to a first row of hair with product composition in reservoir 130 and to a second row of hair with the product composition in reservoir 120, with an intervening row of hair to which the product composition is not applied. This process may be repeated to provide additional streaks and/or highlights to the hair.

The hair bleach product composition is allowed to remain on the hair for a discreet amount of time, depending on the color of the hair being treated and on the desired final shade of the hair. This is generally from about 5 minutes to about one hour, preferably 10 minutes to 45 minutes. When the desired shade is obtained, the hair is shampooed and/or rinsed. At this time any post-treatment composition, e.g., conditioner, etc. may be applied to the hair.

Optionally, at least one of the component compositions (a), (b) or (c) in the hair bleach product, or a separate component of the kit, may contain a colorant for use, when the hair bleach product is applied to the hair, as a visual cue to the colorist to indicate where the product is being applied to the hair. The colorant is selected from the group consisting of water insoluble pigments, lakes and mixtures thereof. Preferably, the colorant is present in the powder activator component. In any event, the colorant should be compatible with the other components of the hair bleach product, and in particular compatible with the persulfate, the alkalizer, and especially the oxidizing agent, usually hydrogen peroxide.

Preferably, the colorant is selected from the group consisting of water insoluble pigments or lakes and mixtures thereof (hereinafter "pigment") and is present in the powder activator component, generally in an amount of up to about 2.5% by weight of the powder activator component, preferably from about 0.1 to about 2% by weight. The pigment should be compatible with the other ingredients in the hair bleach product, and in particular it should be compatible with hydrogen peroxide. The pigment imparts to the hair bleach product a color that is visible when the product is applied to the hair, and thus imparts a visual cue to the hair colorist as to where the product is being applied. Suitable pigments include ultramarine blue, D&C Yellow No. 10 aluminum lake, chromium oxide green, titanium dioxide, D&C Red No. 30 lake, and D&C Yellow No. 5 zirconium lake.

Product Manufacture

The hair bleach product of the present invention is made by conventional processes known in the art for making hair bleach products, and comprises admixing the ingredients of each of the component compositions in suitable vessels, followed by packaging in appropriate individual containers.

The present invention is further illustrated by the examples that follow. Unless otherwise indicated all percentages referred to herein are percent by weight on an active ingredient basis of the component compositions or of the mixed bleach product composition, as the case may be.

EXAMPLES

The composition of Examples 1 through 4 are prepared. Each product on a weight basis comprises 4 parts of the developer component, 1 part of the powder activator component, and 2 parts of the alkalizing agent component.

The hair bleach product of each Example 1 to 4 is applied to the hair of a consumer in accordance with the highlighting process previously described in the section "Use of the Bleach Product" and using the applicator, e.g., as described in the section "The Applicator" and illustrated in FIGS. 1 through 4. After 45 minutes the product is shampooed from the hair, which have blonde highlights.

| Components* | Example 1 Weight % | Example 2 Weight % | Example 3 Weight % | Example 4 Weight % |
|---|---|---|---|---|
| Developer Component | | | | |
| Hydrogen Peroxide (50% active) | 18.3 | 18.3 | 18.3 | 18.3 |
| Water | 73.85 | 73.85 | 73.85 | 73.849 |
| Glyceryl Stearate | 3.63 | 3.63 | 3.63 | 3.63 |
| Ceteayl Alcohol | 0.965 | 0.965 | 0.965 | 0.965 |
| Ceteareth-20 | 0.322 | 0.322 | 0.322 | 0.322 |
| PEG-75 Lanolin (50% active) | 0.74 | 0.74 | 0.74 | 0.74 |
| Wax | 0.73 | 0.73 | 0.73 | 0.73 |
| Stearamidopropyl Dimethylamine | 0.6 | 0.6 | 0.6 | 0.6 |
| Etidronic Acid (60% active) | 0.27 | 0.27 | 0.27 | 0.27 |
| Oleth-10 | 0.25 | 0.25 | 0.25 | 0.25 |
| Oleth-2 | 0.25 | 0.25 | 0.25 | 0.25 |
| Simethicone | 0.1 | 0.1 | 0.1 | 0.1 |
| | 100.0 | 100.0 | 100.0 | 100.0 |
| Activator Powder Component | | | | |
| Potassium Persulfate (98.4% active) | 56 | 60 | 39 | 60 |
| Sodium Persulfate (98.4% active) | 3 | | | |
| Ammonium persulfate (98% active) | | | 19 | 20 |
| Silica | 2.7 | 2.7 | 2.75 | 1.6 |
| Sodium Lauryl Sulfate | 1 | 1 | 1 | 1.2 |
| Ultramarine Blue | 1 | 0.5 | 1.5 | 2 |
| Disodium EDTA | 1 | 1 | 1 | 1.2 |
| Sodium Silicate | 35.3 | 34.8 | 35.75 | 14 |
| | 100.0 | 100.0 | 100.0 | 100.0 |
| Alkalizing Agent Component | | | | |
| Water | Q.S. | Q.S. | Q.S. | Q.S. |
| Ethanolamine | 6 | | | 18 |
| Soytrimonium Chloride | 5.85 | 5.85 | 5.85 | 5.85 |
| Propylene Glycol | 12.375 | 13.875 | 13.875 | 13.875 |
| Steareth-21 | 2 | 2 | 2 | 2 |
| Oleamide MIPA | 1 | 1 | 1 | 1 |
| Erythorbic Acid | 0.4 | 0.4 | 0.4 | 0.4 |
| Sodium sulfite | 0.1 | 0.1 | 0.1 | 0.1 |
| EDTA | 0.2 | 0.2 | 0.2 | 0.2 |
| C12–15 Pareth-3 | 5.4 | 5.4 | 5.4 | 5.4 |

-continued

| Components* | Example 1 Weight % | Example 2 Weight % | Example 3 Weight % | Example 4 Weight % |
|---|---|---|---|---|
| C11–15 Pareth-9 (90% active) | 0.7 | 0.7 | 0.7 | 0.7 |
| Oleic Acid | 4.365 | 4.365 | 4.365 | 4.365 |
| Ammonium Hydroxide (28% active) | 12 | 8 | 15 | |
| Botanical Extracts | 0.14 | 0.14 | 0.14 | 0.14 |
| Fragrance | 1.475 | 1.575 | 1.575 | 1.575 |
| Ethoxydiglycol | 2.915 | 2.915 | 2.915 | 2.915 |
| Cocamidopropyl Betaine (30% active) | 2.915 | 2.915 | 2.915 | 2.915 |
| PEG-150/Stearyl/SMDI Copolymer (19% active) | 2.665 | 2.665 | 2.665 | 2.665 |
| | 100 | 100 | 100 | 100 |

*Activity on weight percent basis.

What is claimed is:

1. A hair bleach product in kit form comprising:
   (A) a hair bleaching system comprising:
      (a) a peroxide-based developer component containing by weight of the developer component from about 3 to about 15% hydrogen peroxide
      (b) a powder activator component comprising by weight of the activator powder component from about 40 to about 80% of an alkali metal persulfate selected from the group consisting of sodium persulfate, potassium persulfate, ammonium persulfate, and mixtures thereof, and
      (c) an alkalizing agent component comprising in an aqueous vehicle by weight of the alkalizing agent component, from about 3 to about 25% of an alkalizing agent,
      the components (a), (b) and (c) being adapted for admixture to form a hair bleach product composition intended for application to the hair of a consumer, said hair bleach product composition having a thixotropic rheology and a viscosity of from about 20,000 to about 60,000 cps. at 25° C. and atmospheric pressure, and
   (B) an applicator comprising a handle, at least one head at the distal end of said handle, and at least one reservoir, said reservoir being a substantially open volumetric space defined by a plurality of tines extending outwardly from said head,
   whereby the hair bleach product composition, when contained in the reservoir, is essentially nonflowing in the absence of shear, and is shear thinned when the reservoir containing the hair bleach product composition is pulled through the hair to deposit the hair bleach product composition on the hair.

2. The hair bleach product of claim 1 wherein the developer contains about 6 to 12% hydrogen peroxide.

3. The hair bleach product of claim 1 wherein the alkalizing agent component is selected from the group consisting of ammonium hydroxide and monoethanolamine.

4. The hair bleach product of claim 3 wherein the alkalizing agent component is ammonium hydroxide present in an amount of from about 3 to about 15% measured as a 28% solution.

5. The hair bleach product of claim 1 wherein the developer component has a viscosity of from about 5,000 to about 30,000 cps. at 25° C. and atmospheric pressure.

6. The hair bleach product of claim 1 wherein the alkalizing agent component is in the form of a cream having a viscosity of from about 100,000 to about 500,000 cps. at 25° C. and atmospheric pressure.

7. The hair bleach product of claim 1 wherein the hair bleach product composition obtained by admixture of the components (a), (b) and (c) and as it is applied to the hair, contains on a weight basis: (i) from about 3 to about 7.5% hydrogen peroxide; (ii) from about 3 to about 12% by weight alkali metal persulfate; and (iii) from about 2.5 to about 7.5% alkalizing agent.

8. The hair bleach product of claim 7 wherein the plurality of tines defines two or more opposed planar spaces.

9. A method of bleaching hair, said method comprising the steps of:
   (i) mixing components (a), (b), and (c) of the hair bleach system of claim 1 to form a hair bleach product composition having a thixotropic rheology and a viscosity of from about 20,000 to about 60,000 cps. at 25° C. and atmospheric pressure;
   (ii) providing an applicator comprising a handle, at least one head at the distal end of said handle, and at least one reservoir, said reservoir being a substantially open volumetric space defined by a plurality of tines extending outwardly from said head;
   (iii) placing an amount of the hair bleach product composition into the reservoir, wherein the hair bleach product composition is essentially nonflowing in the absence of shear;
   (iv) applying the hair bleach product composition to the hair, wherein the hair bleach product composition is shear thinned by passing the reservoir containing the hair bleach product composition through the hair;
   (v) contacting the hair with the hair bleach product composition for a period of time effective to lighten the hair; and
   (vi) removing the hair bleach product composition from the hair.

10. The method of claim 9 wherein the plurality of tines defines two or more opposed planar spaces, the hair being treated passing sequentially through a pair of opposed planar spaces when the hair bleach product is applied to the hair.

11. The method of claim 8 wherein the applicator has two reservoirs, there being a space between said reservoirs.

12. A hair bleach applicator comprising a handle, a head at the distal end of the handle, and at least two reservoirs, each of said reservoirs being a substantially open volumetric space defined by a plurality of tines extending outwardly from said head and containing a hair bleach product composition comprising a mixture of the components (a), (b) and (c) as defined in claim 1 that contains on a weight basis: (i) from about 3 to about 7.5% hydrogen peroxide; (ii) from about 3 to about 12% by weight alkali metal persulfate; and (iii) from about 2.5 to about 7.5% alkalizing agent, the hair bleach product composition having a thixotropic rheology and a viscosity of from about 20,000 to about 60,000 cps. at 25° C. and atmospheric pressure, wherein the hair bleach product composition is essentially nonflowing in the absence of shear and is shear thinned when each of said reservoirs containing the hair bleach product composition is pulled through the hair to deposit the hair bleach product composition on the hair.

13. The hair bleach product of claim 1 further comprising in an additional component, or wherein at least one of the components (a), (b), or (c) of the hair bleaching system further comprises, a visual cue colorant selected from the group consisting of water insoluble pigments, lakes, and mixtures thereof.

14. The hair bleach product of claim 13 wherein the visual cue colorant is selected from the group consisting of ultramarine blue, D&C Yellow No. 10 aluminum lake, chromium oxide green, titanium dioxide, D&C Red No. 30 lake, and D&C Yellow No. 5 zirconium lake.

15. The hair bleach product of claim 13 wherein the visual cue colorant is present in the powder activator component.

16. The hair bleach product of claim 15 wherein the visual cue colorant is present in an amount from about 0.1 to about 2.5% by weight of the powder activator component.

* * * * *